(12) United States Patent
Grof et al.

(10) Patent No.: US 11,320,384 B2
(45) Date of Patent: May 3, 2022

(54) METHOD FOR MARKING AND AUTHENTICATING DIAMONDS AND PRECIOUS STONES

(71) Applicants: SOREQ NUCLEAR RESEARCH CENTER, Yavne (IL); SECURITY MATTERS LTD., D.N. Hevel Eilot (IL)

(72) Inventors: Yair Grof, Rehovot (IL); Tzemah Kislev, Mazkeret Bathya (IL); Nadav Yoran, Tel Aviv (IL); Haggai Alon, Kibbutz Naan (IL); Mor Kaplinsky, Herzliya (IL)

(73) Assignees: SOREQ NUCLEAR RESEARCH CENTER, Yavne (IL); SECURITY MATTERS LTD., D.N. Hevel Eilot (IL); YAHIOMA TECHNOLOGIES INC., Vancouver (CA)

(*) Notice: Subject to any disclaimer, the term of this patent is extended or adjusted under 35 U.S.C. 154(b) by 417 days.

(21) Appl. No.: 16/328,526

(22) PCT Filed: Aug. 29, 2017

(86) PCT No.: PCT/IL2017/050961
§ 371 (c)(1),
(2) Date: Feb. 26, 2019

(87) PCT Pub. No.: WO2018/042427
PCT Pub. Date: Mar. 8, 2018

(65) Prior Publication Data
US 2019/0187063 A1 Jun. 20, 2019

Related U.S. Application Data

(60) Provisional application No. 62/381,243, filed on Aug. 30, 2016.

(51) Int. Cl.
*C23C 16/455* (2006.01)
*G01N 21/87* (2006.01)
(Continued)

(52) U.S. Cl.
CPC ............... *G01N 21/87* (2013.01); *B28D 5/00* (2013.01); *G01N 23/223* (2013.01);
(Continued)

(58) Field of Classification Search
None
See application file for complete search history.

(56) References Cited

U.S. PATENT DOCUMENTS

| 4,392,476 A | 7/1983 | Gresser et al. |
| 2003/0194052 A1 | 10/2003 | Price et al. |

(Continued)

FOREIGN PATENT DOCUMENTS

| EP | 1630549 A1 | 3/2006 |
| WO | 02/068945 A1 | 9/2002 |

(Continued)

*Primary Examiner* — Shamim Ahmed
*Assistant Examiner* — Bradford M Gates
(74) *Attorney, Agent, or Firm* — Browdy and Neimark, PLLC (57) ABSTRACT

Method and systems are presented for authentication of precious stones, according to their natural ID and/or predetermined markings created in the stones, based on unique characteristic radiation response of the stone to predetermined primary radiation.

11 Claims, 4 Drawing Sheets

(51) Int. Cl.

| | | |
|---|---|---|
| *G01N 23/223* | (2006.01) | |
| *G01N 33/38* | (2006.01) | |
| *B28D 5/00* | (2006.01) | |
| *G06K 19/06* | (2006.01) | |
| *C01B 32/28* | (2017.01) | |
| *C23C 16/28* | (2006.01) | |
| *G01N 21/64* | (2006.01) | |

(52) U.S. Cl.
CPC ..... *G01N 33/381* (2013.01); *G06K 19/06009* (2013.01); *C01B 32/28* (2017.08); *C23C 16/28* (2013.01); *C23C 16/45525* (2013.01); *G01N 2021/6439* (2013.01); *G06K 2207/1012* (2013.01)

(56) References Cited

U.S. PATENT DOCUMENTS

| | | |
|---|---|---|
| 2004/0144761 A1 | 7/2004 | Benderly |
| 2007/0058775 A1 | 3/2007 | Benderly |
| 2013/0130044 A1 | 5/2013 | Maula et al. |
| 2016/0070723 A1 | 3/2016 | Horiuchi |

FOREIGN PATENT DOCUMENTS

| | | |
|---|---|---|
| WO | 2011101724 A2 | 8/2011 |
| WO | 2016092300 A1 | 6/2016 |
| WO | 2016/157185 A1 | 10/2016 |

METHOD FOR MARKING AND AUTHENTICATING DIAMONDS AND PRECIOUS STONES

TECHNOLOGICAL FIELD

The invention is in the field of product authentication techniques, and relates to a method and system for marking and authenticating precious stones and diamonds.

BACKGROUND

Techniques for marking precious stones are generally known. For example, U.S. Patent Publication No. 2007/0058775 discloses a method for authenticating diamonds marked with indicia, such as a serial number, or a logo, which is characterized by incisions or cuts etched in the precious stone by a radiation source such as a laser. A residue of coating material remains in the incisions or cuts, and can be detected using XRF analysis.

US Patent Publication No. 2003/0194052 discloses an apparatus and methods in which one or more elemental taggants that are intrinsically located or extrinsically placed in an object are detected by x-ray fluorescence analysis to identify or track/trace the object or its point of manufacture, as well as to establish the origin of objects and their authenticity. The taggant could be incorporated in an object in a number of processes, such as abrasive blasting process by placing the taggant in the abrasive material, and by placing the taggant in the deposition materials during a thin film deposition process for making 2d labels.

GENERAL DESCRIPTION

The present invention provides a novel, relatively simple, technique for marking precious stones, such as diamonds, both rough and polished/cut, enabling authentication of the precious stones. The marking technique of the invention utilizes deposition of a predetermined unique material composition (one or more predetermined materials) onto any surface of the stone (up to the entire surface), which can be detected by X-Ray Fluorescence (XRF) analysis.

The invention, in its another aspect, provides a novel authentication technique for authenticating precious stones, in particular diamonds, in the natural state thereof, i.e. without a need to induce any specific marking to the stone.

The novel marking technique of the present invention is non-distractive so as not to induce any surface relief, and provides a so-called "invisible" marking so as not to affect the appearance of the stone (the stone characteristics, e.g. color, reflection, refraction), thereby not affecting the value of the precious stone. The properties of the marking/coating (e.g. the X-Ray fluorescence response) is durable and resilient.

It should be understood that applying a non-distractive marking to precious stones, and in particular, diamonds. is challenging, inter alia, due to the following factors:

During and after the processes of cutting and polishing, diamonds undergo aggressive cleaning processes, such as regular boiling and deep boiling (or deep cooking). The regular boiling process is aimed at dissolving external dirt; during this process diamond is placed in a mixture of sulfuric acid and potassium chloride and 'boiled' for about 15 minutes or more. Deep boiling (or deep cooking) process is aimed at for removing black graphite dots trapped under the surface of diamonds and which may be accessed via tiny natural cracks in the diamond surface (or holes drilled using lasers). During this process, the diamond is placed in a mixture of extremely strong acids in high temperature (over 300° C.) and high pressure, for a period of 10-12 hours. Thus, the marking applied to precious stones (e.g. diamond) should be durable and resilient, namely it withstands such aggressive cleaning processes.

Further, the surface of some of precious stones and especially diamonds (particularly in the case of polished diamonds) is smooth and is of relatively non-active nature, making it difficult to attach a marker to such surface (and in particular provide attachment which is resilient and durable).

Also, it is desirable that marking applied to a precious stone (diamond) does not induce any damage to the diamond, i.e. does not affect its geometrical, mechanical and optical properties. More specifically, marking of stone should avoid introduction of any surface relief (permanent features such as protrusions, recesses or inscriptions on its surface) to maintain the desired smoothness of the surface of the stone and geometrical features of the stone. The marking should not affect the stone's properties in any other manner (as is the case for example with laser inscriptions), in particular, the marking should be completely invisible (even under inspection by a loupe or other optical means), and should not affect the optical properties (transparency, translucency, refractivity, and colour) of the stone.

Considering diamonds, it is known to classify diamonds by a so-called "4Cs" diamond quality conditions defining the diamond value. These include: carat (weight), clarity (amount and type/size of impurities), color, and cut (shape). The marking technique of the present invention provides for maintaining these 4Cs diamond quality parameters.

The marking technique of the present invention solves the above problems associated with the aggressive cleaning processes during manufacture of stones such as diamonds and with the requirement to maintain the diamond properties. Also, the marking method of the invention is applicable to precious stones of practically any size (from tiny particles up to tens of centimeters) and shape. Additionally, the marking method of the present invention is applicable to precious stones during any one of the manufacturing stages, as well in between the manufacturing stages, and after the stone is complete, from the point of mining to the end client, and in particular to both rough and cut and/or polished diamonds. The marking method can be applied to single crystal or poly-crystal diamonds and to both natural and synthetic diamonds. Therefore, the term diamond should be interpreted broadly covering all these options.

The marking method of the present invention provides full control of the material composition (i.e. concentration of the marking elements) attached to the surface of the diamond, enabling fast and accurate detection of the marking (in verification an authentication procedures).

Also, the invention provides for use of multiple different markings applied to the precious stone at different stages, for example for the purposes of encoding different information at each step. Such multiple different markings may present a coding system, wherein the type and different concentrations of the markers are determined according to a preselected code, e.g. code-word or multi-bit code.

As indicated above, the invention also provides for characterizing and authenticating a diamond (or any other precious stone) in its natural state, i.e. without the use of previously induced signature or marking. The inventors have found that diamond typically includes various "foreign" materials (e.g. impurities in the carbon crystal structure of the diamond) which may exist naturally on the surface or throughout the bulk of the diamond, and thus "natural elemental ID" may serve as a unique characteristic of a precious stone or to a batch of stones. Such natural elemental ID may be used to indicate particular diamond/stone or the source of the stone or the chain of supply stone, e.g. identifying the geographical location from which the precious stone was mined, or for encoding any other data as required.

The marking, as well as natural elemental ID, can be detected/identified using XRF analysis. The elemental ID is determined by the presence and concentration of various 'foreign' materials (e.g. impurities in the carbon crystal structure of the diamond) throughout the bulk of the precious stone (i.e. being naturally embedded in the stone). It should be understood that the unique characteristic response of the stone being marked by predetermined marking(s) is a result/depends on the marking(s) (material compositions, concentrations, etc.) and the surface/structure of the specific stone on which said markings has been created.

Thus, according to one aspect of the invention, there is provided a method for use in marking precious stones to enable authentication of the precious stones. The method comprises: applying a material deposition process to the precious stone and creating at least one predetermined marking on at least a portion of a surface of the precious stone, said at least predetermined marking being unique for said precious stone or a batch of related precious stones, such that the precious stone with said at least one predetermined marking is characterized by unique characteristic X-ray or gamma-ray radiation response to predetermined primary radiation, thereby enabling to authenticate the precious stone upon identifying the unique characteristic radiation response of the stone.

The predetermined marking is in the form of a single- or multi-layer continuous film. The unique characteristic X-ray or gamma-ray radiation response is indicative of a unique material composition of said at least one predetermined marking, defined by materials and materials' concentrations of the marking.

Preferably, the unique characteristic X-ray or gamma-ray radiation response of said at least one predetermined marking being created is read for verification purposes and/or for recording data indicative of the unique response for further identification/authentication procedures. The verification comprises: applying predetermined primary radiation to said at least portion of the stone to induce secondary radiation from said at least portion of the stone in response to said primary radiation, and detecting the secondary radiation and recording data indicative thereof, enabling storage of data/signature of the unique characteristic radiation response; and further analysis of detected secondary radiation to identify whether the detected secondary radiation matches the predetermined characteristic radiation response.

The invention also provides a system for surface treatment of precious stones to allow authentication of the stone. The system comprises: a material deposition unit configured and operable for applying the above described material deposition process to the precious stone and creating the at least one predetermined marking on at least a portion of a surface of the precious stone; and a control system configured and operable to control operation of the material deposition system to create said at least one predetermined marking and for performing the above described verification of the at least one predetermined marking being created.

The invention, in its another aspect, provides a method for authenticating a precious stone. The method comprises: applying predetermined primary radiation to at least portion a portion of the stone to induce secondary radiation from said at least portion of the stone in response to said primary radiation; detecting the secondary radiation response and generating measured data indicative thereof; analyzing said measured data using reference data about various precious stones and their unique characteristic responses to said primary radiation stored in a database, for determining a match between the measured data and data in said database, and generating notification data indicative of whether the stone has been identified or not.

In some embodiments, the unique characteristic response corresponds to unique material composition of a marking carried by the stone. In some other embodiments, the unique characteristic response corresponds to natural elemental ID of the stone defined by material composition of the stone resulting from the stone natural formation process. The natural elemental ID may also depend on the manufacture (i.e. sawing and/or cutting) of the stone.

The invention also provides an authentication system for use in authenticating a precious stone. The system comprises a reading unit, and a control system. The reading unit is configured and operable similar to the above described verification unit, for applying predetermined primary radiation to at least portion a portion of the stone to induce secondary radiation from said at least portion of the stone in response to said primary radiation, detecting the secondary radiation response and generating measured data indicative thereof. The control system is configured and operable for analyzing said measured data using reference data about various precious stones and their unique characteristic responses to said primary radiation stored in a database, for determining a match between the measured data and data in said database, and generating notification data indicative of whether the stone has been authenticated or not.

The invention also provides a precious stone structure comprising a precious stone having pre-marking original values for a predetermined set of parameters of the precious stone uniquely characterizing said precious stone, and one or more markings located on at least a portion of a surface of the precious stone, said precious stone structure having values for said predetermined set of parameters which are substantially equal to said original values.

In its yet further aspect, the invention provides a diamond structure comprising a diamond characterized by pre-marking original values of carat, clarity, color and cut of the diamond, and one or more markings located on at least a portion of a surface of the diamond, said diamond structure having carat, clarity, color and cut values substantially equal to said original values.

The invention, in its another aspect, provides a novel method for constructing a precious stones database, and the resulting novel precious stones database. According to this method, a precious stone after being manufactured/prepared for further use is "measured" by applying thereto primary X-ray or gamma ray radiation, detecting a secondary radiation from the stone in response to said primary radiation, applying spectral analysis to data indicative of said secondary radiation response, and determining a unique spectral signature of the precious stone. The unique spectral signature of the precious stone is actually a spectral signature of foreign material composition embedded in said precious stone, which is unique for said stone or a batch/group of similar stones resulting from the natural formation process as well as said manufacture. The spectral signature includes data about at least a few (e.g. 4 or more) foreign materials, each such material being characterized by predetermined two or more conditions/parameters, e.g. relative to the other foreign material. These conditions/parameters may include at least relative concentration of the respective foreign material and relative spectral response of said foreign material (e.g. relative number of characteristic spectral peaks associated with the presence of said material relative to at least one other foreign material). The unique spectral signature is stored in the database as natural elemental ID assigned to the precious stone, i.e. to unique foreign material composition embedded in said precious stone. This stone can therefore be authenticated based on the secondary radiation response thereof.

The invention also provides a precious stone kit comprising a precious stone and a certificate assigned to said precious stone, wherein said certificate comprises a natural elemental ID assigned to unique foreign material composition of said precious stone, and the precious stone is responsive to a predetermined primary radiation by a unique secondary radiation response carrying a radiation signature indicative of the foreign material composition of said precious stone, thereby enabling authentication of the precious stone upon identifying a match between said natural elemental ID in the precious stone's certificate and the radiation signature.

The invention further provides an authentication system for use in authenticating precious stones, such as diamonds, the system comprising: a reading unit, and a control system, wherein the reading unit is configured and operable for applying predetermined primary radiation to at least portion a portion of the diamond to induce secondary radiation from said at least portion of the diamond in response to said primary radiation, detecting the secondary radiation response and generating measured data comprising a radiation signature of the diamond indicative of material composition of said diamond; and the control system is configured and operable for data communication with an analyzer to generate an output signal indicative of whether said radiation signature of the diamond satisfies a matching condition with natural elemental ID assigned to unique material composition of said diamond and recorded in the diamond certificate.

In its further aspect, the invention provides a storage device (database) configured to be accessible via a communication network, the storage device comprising: a plurality of electronic certificates assigned to a respective plurality of precious stones, such as diamonds, or plurality of groups of precious stones (diamonds), each of the electronic certificates comprising a natural elemental ID assigned to unique material composition of the respective precious stone or group of precious stones and data indicative of a corresponding unique radiation signature of the precious stone or group of precious stones.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The invention, in its some aspects, provides a marking method and system for use in marking precious stones in manner to create an X-ray based detectable marker on stone, wherein the marker as well as marking process do not affect any of geometrical, mechanical and optical properties of the stone providing that the quality (value) of the stone is not affected, and also do not affect the standard manufacturing process of the stones, while providing resilient and durable attachment of the marker to the stone.

More specifically, the present invention is used for marking and authenticating diamonds and is therefore exemplified below with respect to this specific application. It should, however, be noted that the principles of the present invention are not limited to this specific application, and can be used with any type (as well as size and shape) of precious stones.

In the invention, the marker is applied to the surface of a diamond using vacuum deposition methods, preferably those in which single atom (or single molecule) layers of one or more marking elements ("markers") and optionally additional materials are deposited on the surface of the diamond. The deposition process is carried out at pressure which is well below atmospheric pressure or in vacuum (i.e. in a vacuum chamber). In general, vacuum deposition processes enable the deposition of layers which range in thickness from single atom up to a few millimeters. The material being deposited on a substrate in such methods is in vapor state.

It should be noted that the term marking element or marker as used herein refers to an element which can be identified by XRF analysis, namely, element which responds to exciting X-ray or gamma-ray radiation (primary radiation) by emission of an X-ray response signal (secondary radiation or excited radiation) with spectral features (i.e. peaks in particular wavelength(s)) which characterize the element. In the description below, such an X-ray response signal is referred to as XRF signature.

Preferably, the vacuum deposition process used in the marking technique of the invention utilizes Atomic Layer Deposition (ALD), being based on the principles of Chemical Vapor Deposition (CVD) in which the vapor is generated by chemical reactions which include one or more precursors. The category of CVD includes various processes such as low-pressure chemical vapor deposition (LPCVD), Plasma-Enhanced Chemical Vapor Deposition (PECVD), Plasma-Assisted CVD (PACVD), and Atomic Layer Deposition (ALD).

Alternatively, or additionally, the process of depositing the marker material(s) on the diamond includes Physical Vapor Deposition (PVD) in which the vapor source is solid or liquid. A PVD process may use techniques such as sputtering, cathodic arc deposition, thermal evaporation, laser ablation serving as a (solid) precursor to generate vapor, and electron beam deposition, to generate the deposited particles in a vapor phase.

Figure 1:
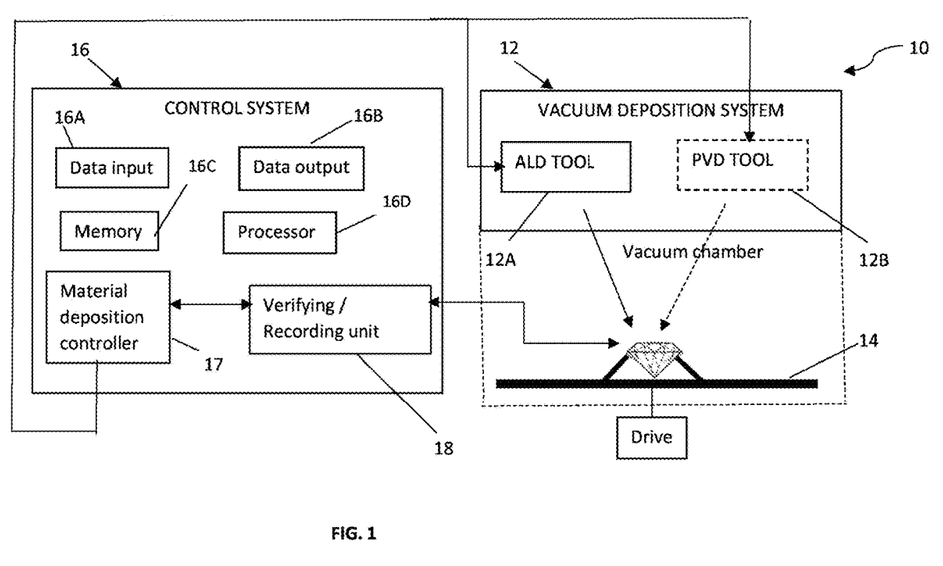
FIG. 1 is a block diagram exemplifying a marking system according to the invention for marking precious stones.

FIG. 1 schematically illustrates, by way of a block diagram, the marking system 10 of the invention. The system 10 includes such main functional parts as a material deposition system 12 associated with a stone holding unit (stage, e.g. X-Y or R-Theta movable stage) 14, and a control system 16 connectable (via wires or wireless signal transmission) to the material deposition system 12, and possibly also to the stage 14 (i.e. its driver in case the relative displacement of the stage with respect to the processing tool of system 12 is considered). In the present not limiting example, the material deposition system 12 includes an ALD tool 12A and possibly also a PVD tool 12B.

The control system 16 is appropriately configured and operable for controlling the material deposition process being performed by the system 12 to provide desired material composition of the marker(s) and desired marker-film thickness. The control system 16 is typically a computer system including inter alia such functional utilities as data input and output utilities 16A and 16B, memory 16C, processor utility 16D, and also includes a material deposition controller 17 (receiving user input about the marker(s) to be created and generating corresponding operating parameters to the processing (material depositing) tool. Preferably, the control system 16 also includes a recording unit 18, which is configured as an XRF reader for reading the marker(s) being formed in the stone, such as an Energy Dispersive XRF (EDXRF) analyzer. The recording unit 18 is configured for applying to the precious stone (or at least portion thereof where the marking is being created) predetermined primary radiation (X-ray or gamma-ray radiation) to thereby induce secondary radiation from the stone (or at least the respective portion thereof) in response to the primary radiation, and detecting the secondary radiation, and verifying/recording data indicative thereof. This data is stored in the memory 16C and/or in a remote storage device (database) as the data/signature corresponding to the unique characteristic radiation response of the specific stone or a group/batch of related stones, to be further used during verification/authentication procedure.

The operation of the ALD and/or PVD based systems are generally known, and therefore need not be described in details. The system operation to implement the method of the invention is exemplified more specifically further below.

The vacuum deposition method of the present invention allows for depositing a layered structure carrying one or markings, e.g. uniform overall layers of compounds (including markers) over the surface of a precious stone, e.g. a continuous (unpatterned) layered structure/film or layered structure/film formed by discrete spaced-apart regions of the deposited compounds (being deposited via a mask). It should be noted that using the ALD as a material deposition method, provides for the overall depositing layer on the entire surface of the diamond exposed to the material being deposited (except for the points or area of contact with a sample tray or other holding means) to be completely uniform up to a single molecule level. The other CVD based techniques provides the layer uniformity up to some statistical deviation. As for the PVD, this technique provides mainly for creating a uniform overall layer on the surface that is facing the precursor (depending on the particular method). Thus, the uniformity of the overall layer depends on the particular method of deposition: in ALD the overall layer is formed all over the surface uniformly except for the points of contact with a holding means; in CVD not as much; and in PVD the uniform layer can be formed mainly on the surfaces which directly faces the precursor.

The uniformity of the layer facilitates fast and accurate measurement of the concentration of deposited markers. For example, the measured concentration is, to a high degree, constant over the entire surface of the precious stone, or over the entire surface region of the stone where the marker(s) is/are placed.

In order to apply one or more markers to the surface of a diamond, such that the marking does not affect the appearance or other properties of the diamond (as described above), an ultra-thin marking layered structure is created ranging in thickness from a single angstrom (that is a single atom or single molecule) to hundreds or thousands of angstroms. In an example, the thickness of the deposited layered structure is between 50 angstroms and 150 angstroms.

The thickness of the film-marker may be determined by the type of precious stone which is to be marked. For example, marking of rough diamonds may be obtained with a thinner marking layer as compared to cut or polished stone due do its rough surface.

Figure 2A:
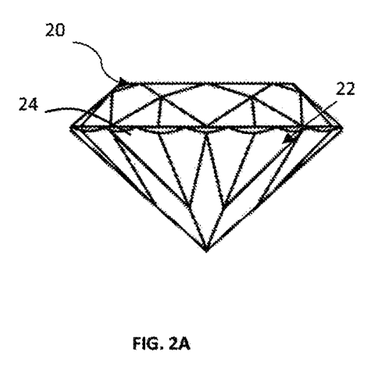
FIGS. 2A and 2B exemplify a diamond carrying invisible and properties-maintaining marking of the invention.
Figure 2B:
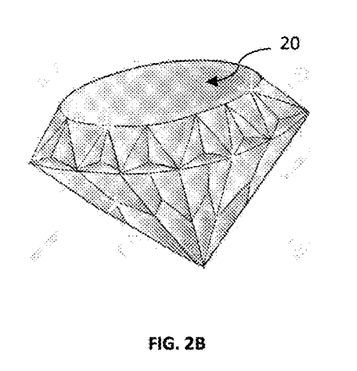

As indicated above, the marker being created is in the form of an invisible film (layered structure). This is schematically demonstrated in FIG. 2A, showing a diamond 20 (generally, a precious stone) being in this non-limiting example a cut and polished diamond 20 having an arrangement of facets. The diamond has its unique combination of a set of parameters having original values. The marker in the form of invisible film, having unique XRF response (secondary radiation induced in response to incident primary radiation), may be located on the entire surface 22 of the diamond, or only on part thereof, e.g. on one of its facets 24, as the case may be. FIG. 2B demonstrates that the properties of the diamond (i.e. values of said parameters) are not affected by the marker carried by the diamond. As indicated above, diamond is typically classified by its carat, clarity, color and cut. The inventors have shown that inducing one or more markings of the present invention on at least a portion of the diamond's surface provides for maintaining the original (pre-marking) values of these parameters.

Additionally, the method of the present invention allows the deposition of ultra-thin marking layers which can be detected only by utilizing advanced methods for amplifying and enhancing the XRF signals emitted by the markers. For example, the methods described in International application PCT/IL2016/050340, which is assigned to the assignee of the present application and is incorporated herein by reference.

Figure 3A:
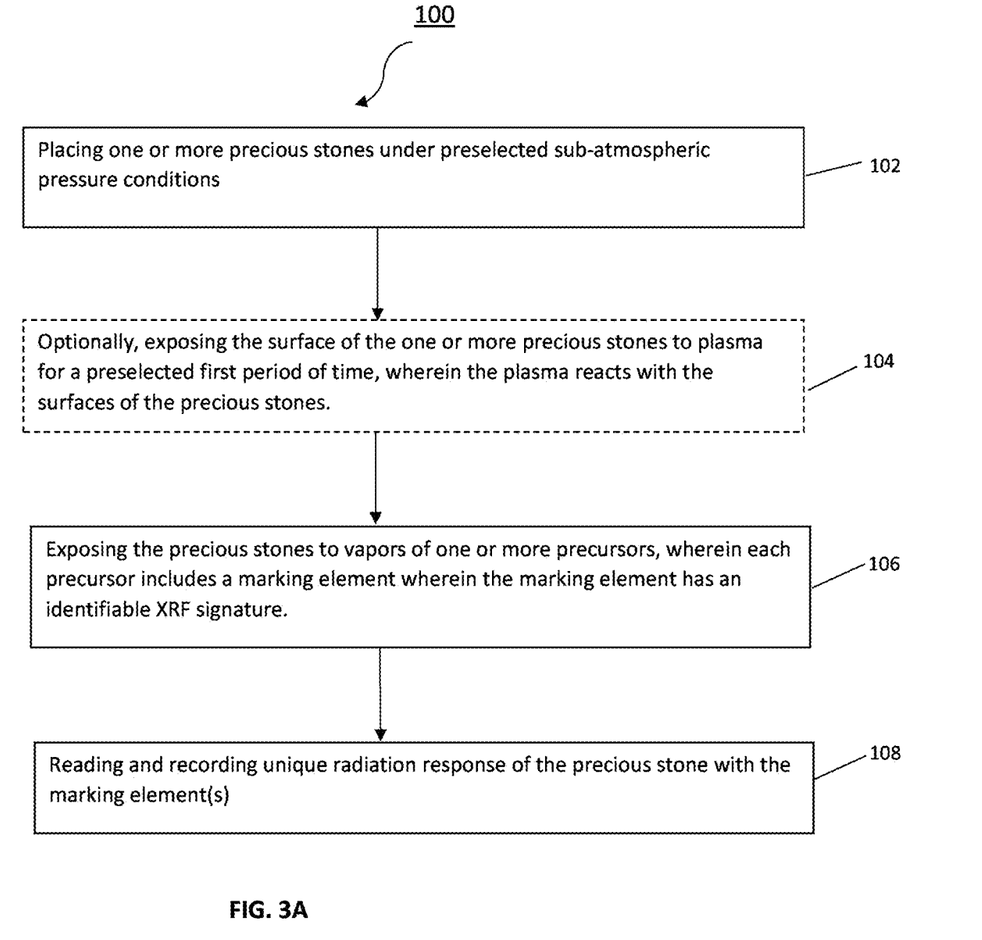
FIGS. 3A and 3B show flow diagrams of two examples, respectively, of a method of the invention for marking precious stones.

Reference is now made to FIG. 3A which is a flow diagram 100 of a method (carried out by the marking system similar to that described above with reference to FIG. 1) for marking precious stones according to an embodiment of the present invention. The marking according to this method allows the authentication of the precious stones by detecting the marking using XRF analysis. In procedure 102, one or more precious stones to be marked are placed under preselected high temperature and sub-atmospheric pressure conditions (e.g. in a vacuum chamber). In optional procedure 104, the surfaces of the precious stones are treated by plasma. For example, the surfaces of the precious stones may be treated by oxygen or water plasma, which may bond OH (hydroxyl) groups to the surface of the precious stones. In procedure 106, the precious stones are exposed to one or more precursors in a vapor phase for a preselected period of time. The molecules of each of the precursors includes a marking element or marker (namely, an element with an identifiable XRF signature) and may include additional materials. For example, the molecules of the precursors may include organic parts. The marking elements, for example, may be metals. In a different example, the marking elements may be non-metals such as halogens. The exposure of the precious stones to the precursors enables the attachment of the precursor molecules and the markers to the surfaces of the precious stones. In an example, the precursors vapor may react with the OH groups which may exist (either naturally, or due to the plasma surface treatment) on the surface of the precious stone. Furthermore, monolayers of molecules (that is, layers which are one molecule thick) which include the markers are constructed over the surfaces of the precious stones. The number of layers and consequently, the thickness of the overall layer (including all monolayers) is determined by the time of exposure of the precious stones to the precursors vapor. Alternatively, in a self-terminating process such as ALD, which comprises a plurality of self-saturating cycles, the thickness of the layer is determined by the number of cycles.

In an embodiment of the present invention the deposition of one or more marking elements is carried out using ALD. The vapor which is introduced into the vacuum chamber is generated from one or more precursors in a liquid phase. In an example the precursors are organometallic compounds. The ALD process facilitates the deposition of a uniform pinhole-free film without discontinuities or holes which may be present in film grown via nucleation (as may be the case in other CVD or PVD methods, particularly in very thin films). Additionally, the ALD process may create a practically stress-free film as compared to other deposition methods wherein compressive or tensile stress may cause delamination and separation between the film and the substrate which may result in cracks and blisters. Furthermore, the aspect ratio of the ALD method is very high, for example 2000:1 or higher (namely, with ALD one may create a uniform layer even in cracks and recesses wherein the ratio between the width and the depth of the recess is higher than 2000:1). The high aspect ratio contributes to the uniformity (and consequently the resilience) of the film and additionally allows for a high density marked during a single ALD process.

Then, preferably, the precious stones with the marking created as described above undergoes a so-called "reading procedure" (step 108) for reading and recording the unique characteristic radiation response (X-ray or gamma-ray radiation response) of the stone with marking(s) therein. To this end, the precious stone (or at least portion thereof where the marking has been created) is subjected to predetermined primary radiation to induce secondary radiation from the stone (or at least portion thereof) in response to the primary radiation, and the secondary radiation is detected, and data indicative thereof is recorded, enabling storage of the corresponding data/signature as the unique characteristic radiation response of the specific stone or a group of related stones.

Figure 3B:
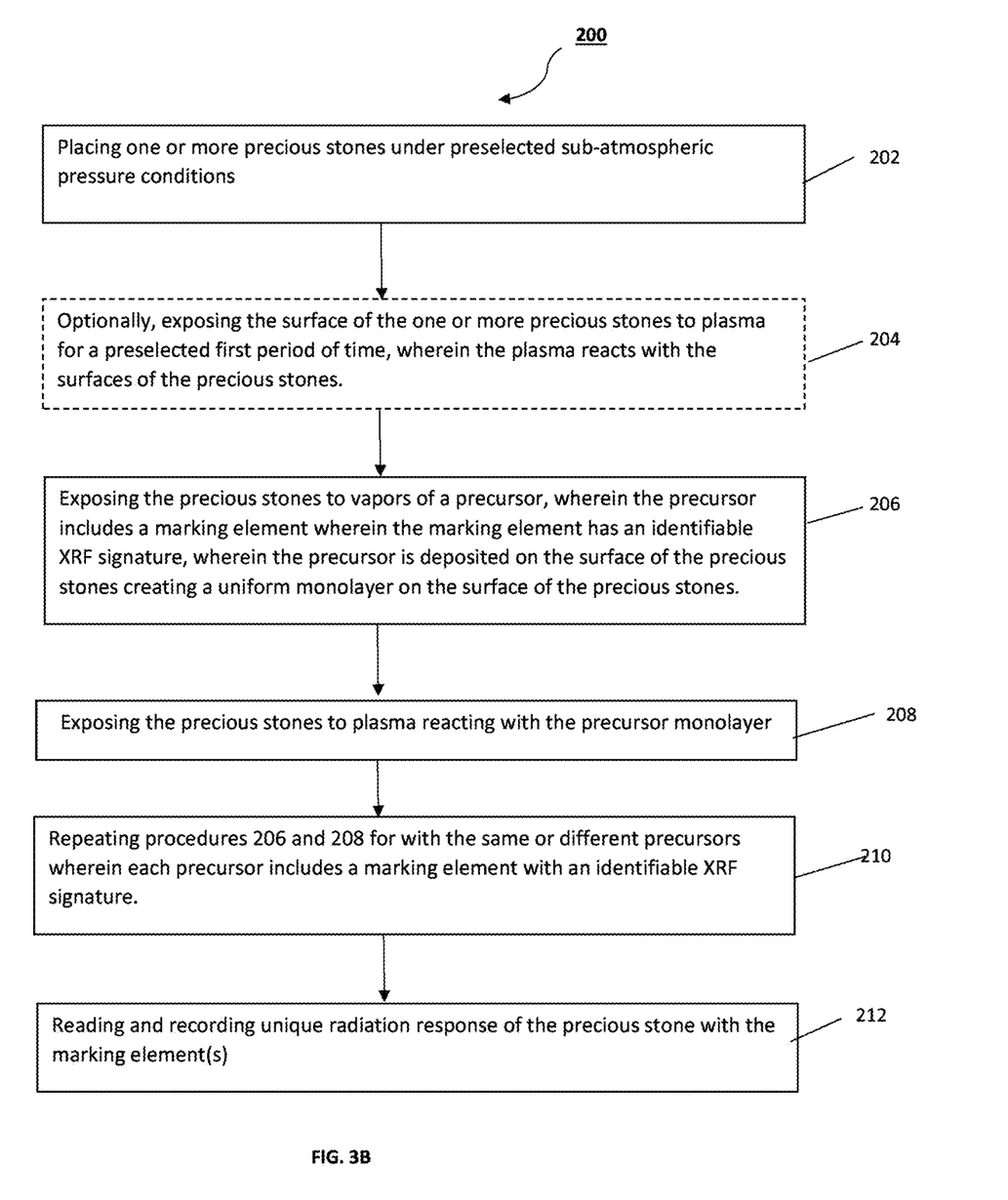

Reference is now made to FIG. 3B which is a flow diagram 200 of a method for marking precious stones according to another embodiment of the present invention. In procedure 202, one or more precious stones to be marked are placed under pre-selected high temperature and sub-atmospheric pressure conditions (e.g. in a vacuum chamber). In optional procedure 204, the surfaces of the precious stones are treated by plasma. For example, the surfaces of the precious stones may be treated by oxygen or water plasma, which may bond OH (hydroxyl) groups to the surface of the precious stones. In procedure 206, the precious stones are exposed a precursor in a vapor phase, wherein the precursor includes a marking element which may be detected and identified using XRF analysis. The precursor may react with OH groups and other materials which exist on the surface of the precious stone thereby creating a uniform monolayer on the surface of the precious stone. This deposition is self-terminating since once the monolayer is created the deposition is terminated and no additional material is deposited. The excess vapor is then evacuated from the vacuum chamber. In procedure 208, the precious stones are exposed to plasma or water vapor which is introduced to the vacuum chamber. The plasma treatment or the exposure to water vapor bonds OH groups to the monolayer deposited in procedure 206. In procedure 210, procedures 206 and 208 are repeated either with the same precursor and the same marking element or alternatively with a plurality of precursors and a plurality of marking elements. At each step, a uniform monolayer of molecules is created, which include one marking element. The monolayer is then treated with plasma and the next monolayer is constructed.

The overall thickness of the layered structure deposited on the surface of the precious stones in set by the number of cycles, that is the number of deposited monolayers.

Such a layer by layer covalently bonded structure has a number of benefits, for example: XRF marking using such a structure is resilient and wear resistant, and able to withstand the extreme condition of the cleaning processes of diamonds. An additional factor which may contribute to the resilience of the marking are OH groups which may be present on the surface of the diamonds. The XRF marking does not affect the appearance of the diamond due to (i) the small thickness of the structure (possibly down to few angstroms—"ultrathin layer"); and (ii) the use of metallic oxides rather than metals (which are in general more opaque than metallic oxides). The construction of the layer by layer structure allows full control of the thickness of the overall deposited layer (up to a resolution of a single atom) and consequently of the concentration of the one or more markers present on the surface of the diamond which may be detected and measured using XRF analysis. The overall layer is uniform up to an angstrom (the thickness of a monolayer) resolution. The uniformity of the overall layer and the high aspect ratio of the above method contributes to the resilience of the deposited marking due to the lack cracks, pinholes and/or discontinuities in the overall deposited layer, which for example, may expose a cross section of the multi-layered film to the acids and aggressive conditions of a diamond-cleaning processes.

The above method can also be used to deposit a number of marking materials from a number of precursors which are deposited at different pulses. The concentrations of the different markers can be fully controlled by the number of layers of markers deposited on the diamond.

The deposition of a number of markers to the surface of a diamond allows the introduction of a coding system wherein the type and different concentrations of the markers are determined according to a preselected code. A code-word can for example, be used as an elemental ID for the particular diamond or a batch of diamonds, it can be used to indicate the source of the diamond or the chain of supply, or for encoding any other data as required.

Similarly to the above-described example of FIG. 3A, in the example of FIG. 3B the stone with the markings may also undergoes a reading procedure (step 212) for reading and recording the unique characteristic radiation response (X-ray or gamma-ray radiation response) of the stone with marking(s) therein. Such reading and recording procedure is similar to that described above with reference to FIG. 3A.

The following is an example of marking diamonds with metallic-oxides: The diamonds (generally, precious stones) to be marked are also heated by heating the sample tray on which they positioned within the vacuum chamber. The temperature to which the precious stones are heated depends on the particular type of stone, the type of the surface (e.g.

rough or cut) and the type of the precursor. In a particular example, cut diamonds may be heated to 200° C. The precursor is a heated organometallic in a liquid phase. In an example the organometallic compound is heated to 75° C. The deposition is done in cycles (or pulses) wherein in each pulse a one molecule thick layer (monolayer) of metallic oxide is created, initially on the surface of diamond, and thereafter on previously deposited layers.

Each pulse includes two steps. In the first step of the first pulse a layer of the organometallic compound is created on the surface of the diamond wherein the metallic element of each molecule is adjacent to the surface of the diamond and the organic part of each molecule is positioned away from the surface of the diamond. At the end of the first step, the excess vapor is evacuated from the vacuum chamber. In the second step water or oxygen plasma is introduced into the vacuum chamber which removes the organic part of each molecule and bonds one or more OH groups to the metallic element instead. The result of the first pulse is a monolayer of the metallic compound attached to the surface of the diamond, wherein each metallic atom is covalently bonded to OH groups which are positioned away from the surface of the diamond.

In the first step of following pulses, a layer of the organometallic compound is created on the layer of the previous pulse, wherein the metallic element reacts with the OH group of the previous layer creating the covalent bonds M-O-M (M being the metallic element). Namely, the metallic element of the organometallic compound of the new layer becomes covalently bonded to the oxygen atoms of the previous layer, wherein its organic part is position away from the previous layer. At the end of the first step, the excess vapor is evacuated from the vacuum chamber.

In the second step of each of the following pulses, water or oxygen plasma is introduced to the vacuum chamber removing the organic part of the molecules of the previous layer and creating covalent bonds with OH groups instead.

Each pulse therefore creates a monolayer of the metallic compound which is covalently bonded the layer of oxygen atoms of the previous layer (bottom layer) and to oxygen atom of the present pulse (top layer).

In some embodiments of the present invention, an additional step wherein plasma is introduced into the vacuum chamber prior to the first pulse, is carried out. Such a step may 'activate' the surface of the diamond and assists in bonding the first layer to the surface of the diamond.

Figure 4:
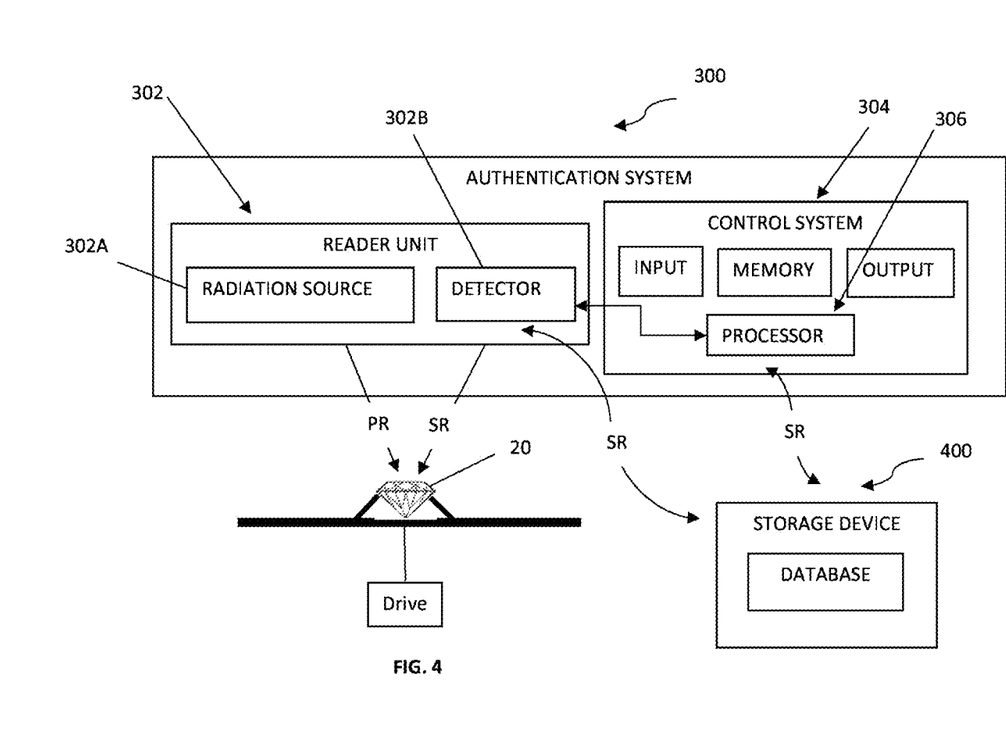
FIG. 4 is a block diagram of an authenticating system according to the invention.

Reference is made to FIG. 4 exemplifying, by way of a block diagram, an authenticating system 300 of the present invention. The authentication system 300 includes a reading unit 302 and a control unit 304 connectable to the output of the reading unit via wires or wireless signal transmission. The reading unit 302 includes a radiation source 302A and a detector 302B. The radiation source 302A is configured to emit an X-ray and/or gamma-ray radiation PR (primary radiation) towards a precious stone 20 under examination. The detector 302B detects a radiation (X-ray) response signal SR (secondary radiation) that is emitted/produced in response from the precious stone ('response signal' or "radiation signature"). The detector 302B generates measured data MD indicative of the detected response signal SR and transmits this data MD to the controller 304. The controller 304 is a computer system including data input and output utilities, memory, etc. The system 300 includes a data processor 306, which is configured to have access to a database which may for example be associated with an external storage device 400, e.g. accessible via a communication network. The database stores information relating to particular (original) precious stones or groups/batches of stones (e.g. unique electronic certificates assigned to the stones/groups of stones) being indicative of material composition characterizing the precious stone/group of stones.

The data stored in the database includes data records/ fields/pieces including data for, respectively, particular precious stones or particular batches/groups of precious stones. In some embodiments, such data per the particular precious stone or particular batch/group of precious stones may include the stone/batch/group characteristic radiation response signal (radiation signature of the stone/group) and the corresponding material composition of the stone/batch/ group.

In some embodiments, the processor 306 may be configured to apply fitting-based processing to the detected radiation response signal SR, and if and when the best matching response signal/radiation signature in the database is found the respective stone is positively authenticated. The control system 304 may generate the notification signal about the authentication results.

The authentication procedure may be based on identification of the stone based on the marking previously induced/ deposited or on the natural elemental ID of the stone, as described above. Accordingly, the characteristic response signal being read is either the marker(s) response or the natural ID response; and the operating parameters of the reading unit 302 (e.g. its operative wavelengths ranges) are adjusted accordingly.

It should be understood that considering authentication based on markers, the data to be identified may generally include presence of a predetermined layered structure on at least a portion of the surface of a precious stone, or may include concentrations of the predetermined materials on the surface of the precious stones, that is, their concentrations in the overall marking layer or layered structure applied to precious stone. The particular markers and their concentrations may be set according to a preselected code wherein each individual precious stone or alternatively a batch of precious stones marked in a single process are allocated a particular code-word.

In a particular example, a diamond may be marked by a uniform film comprised of about 100 monolayers of platinum interspaced with monolayers of oxygen deposited on the diamond's surface using ALD. The diamonds are placed in a vacuum chamber on a sample tray/stage heated to about 100-150° C. At a first stage, the surface of the diamonds is treated with oxygen plasma. An organometallic precursor vapor comprising (Trimethyl)-methylcyclopentadienyl platinum is introduced to vacuum chamber creating a monolayer of platinum on the surface of the diamonds which bonds to the oxygen of OH groups on the surface. In the process the hydrogen atoms are removed from the OH groups and bond to the organic part of the precursor's molecules. The organic part of the precursor's molecule on the diamond surface is positioned away from the surface. The residuals of the precursor vapor are then evacuated from the vacuum chamber, and oxygen plasma is introduced to the chamber removing the organic part of the organometallic precursor and bonding OH groups to the platinum. The process continues in alternate stages of creating interspaced layers of platinum and oxygen. The process continues until a uniform 50-100 angstrom film is deposited on the surface of the diamonds and being covalently bonded thereto. The deposited film is transparent, invisible and does not damage the diamond or affect its value; and the covalent bonding provide a desirably strong and stable attachment of the film to the diamond.

Considering the authentication based on natural elemental ID of precious stones, e.g. diamonds, the following should be noted. The carbon crystal structure of diamonds (diamond lattice) may include various types of impurities and imperfections, that is, various types of foreign metallic or non-metallic particles and materials. These impurities are incorporated throughout the crystal but may be more abundant at the surface of the diamond due to unfulfilled excess valences of the carbon atoms at the end surfaces and the edges of the crystal.

The foreign materials may for example include two or more of the following elements: Ti, Cr, Zn, Ag, Tl, W, Ni, Co, Ta, Si, Mg, P, Cd, V, Fe, Cu, Pb, Mn, Tc, Nd, Y, Ga, Ca, F, As, as well as other elements.

The foreign materials and their concentrations on the outer layer of the diamond can be measured by XRF analysis, wherein the depth or thickness of the outer layer as well as the accuracy of the measurement are determined by the particular XRF analyzer used for analysis. The types of foreign materials and their corresponding concentrations and/or relative concentration may be used as an elemental ID for a particular precious stone (e.g. diamond) or a batch of stones (diamonds). The foreign materials found in the precious stone are typically incorporated or trapped within the core of the precious stone (diamond crystal) during the formation of the crystal. These materials therefore correspond to the environment present at the vicinity of the location where the process of diamond's formation took place. Consequently, such elemental ID may also correspond to the source of the diamond, that is the particular mine, or more generally the geographical region from which it originates.

In an aspect of the present invention, foreign materials composition can be detected/read in a particular surface area of the diamond and the elemental ID therefore corresponds to this particular area. Alternatively, the entire surface area of the diamond may be irradiated and the secondary radiation from the entire surface area of the diamond may be collected (for example by rotating the diamond during the irradiation and detection) and analyzed, such that the elemental ID would correspond to the entire surface or outer layer of the diamond.

The following Table 1 and Table 2 show two examples, respectively, of natural elemental IDs for two exemplary diamonds derived from spectra measured by a 2 kilowatt XRF spectrometer. The diamond on stage is rotated during the measurement and the spectrum includes secondary radiation arriving from the entire surface of the diamond.

In the Tables 1 and 2, column 1 includes the main foreign elements found on the surface of the diamond (not including carbon); column 2 lists the main peaks of the spectrum associated with the respective elements; column 3 lists the main atomic transitions contributing to the respective peaks; column 4 includes the relative area of each peak corresponding to the number of counts associated with the peak (namely, the relative area is the number of counts associated with a peak divided by the total number counts associated with all the peaks for all the foreign elements); and column 5 includes the relative concentration of the foreign elements calculated from the spectrum. The relative concentrations in the Tables include only the main foreign elements and were normalized to 1.

TABLE 1

| Element | Peak-energy [eV] | Atomic state transitions | Relative peak area (relative number of peaks) | Relative concentration |
|---|---|---|---|---|
| N | 373.9 | $K_\alpha$, $K_\beta$ | 0.110827 | 0.110827 |
| Si | 1761.1 | $K_\alpha$, $K_\beta$ | 0.082408 | 0.082408 |
| Ar | 2955.6 | $K_\alpha$ | 0.052162 | 0.097633 |
|  | 3154.9 | $K_\beta$ | 0.04547 |  |
| Ca | 3659 | $K_\alpha$ | 0.02782 | 0.02782 |
| Mn | 5899.9 | $K_\alpha$ | 0.028836 | 0.028836 |
| Fe | 6413.5 | $K_\alpha$ | 0.060483 | 0.08484 |
|  | 7031.8 | $K_\beta$ | 0.024357 |  |
| Ni | 7464.5 | $K_\alpha$ | 0.039696 | 0.039696 |
| Cu | 8038.5 | $K_\alpha$ | 0.059786 | 0.107098 |
|  | 8911.9 | $K_\beta$ | 0.047312 |  |
| Zn | 8619.7 | $K_\alpha$ | 0.049275 | 0.049275 |
| Ga | 9219.4 | $K_\alpha$ | 0.032648 | 0.032648 |
| As | 10523 | $K_\alpha$ | 0.081384 | 0.081384 |
| Kr | 12672.2 | $K_\alpha$ | 0.257537 | 0.257537 |

TABLE 2

| Element | Peak-energy [eV] | Atomic transitions | Relative peak area | Relative concentration |
|---|---|---|---|---|
| F | 710.1 | $K_\alpha$, $K_\beta$ | 0.03278304 | 0.03278304 |
| Ne | 832.9 | $K_\alpha$, $K_\beta$ | 0.0389153 | 0.0389153 |
| Na | 1039.1 | $K_\alpha$, $K_\beta$ | 0.03863866 | 0.03863866 |
| Mg | 1261.1 | $K_\alpha$, $K_\beta$ | 0.02812462 | 0.02812462 |
| Al | 1494 | $K_\alpha$, $K_\beta$ | 0.02069102 | 0.02069102 |
| Si | 1778.7 | $K_\alpha$, $K_\beta$ | 0.01637284 | 0.01637284 |
| Zr | 2116.8 | $L_\alpha$ $L_\beta$ | 0.01368669 | 0.01368669 |
| S | 2350.6 | $K_\alpha$, $K_\beta$ | 0.01266916 | 0.01266916 |
| Cl | 2620.1 | $K_\alpha$, $K_\beta$ | 0.02311165 | 0.02311165 |
| Ar | 2945.6 | $K_\alpha$ | 0.01399434 | 0.02701566 |
|  | 3227.6 | $K_\beta$ | 0.01302132 |  |
| In | 3328.8 | $L_\alpha$ | 0.01269141 | 0.03870782 |
|  | 3459.8 | $L_\beta$ | 0.01282179 |  |
|  | 3876.4 | $L_\gamma$ | 0.01319462 |  |
| Ca | 3705.1 | $K_\alpha$ | 0.01426065 | 0.02469838 |
|  | 4020 | $K_\beta$ | 0.01043772 |  |
| Ti | 4456.3 | $K_\alpha$ | 0.01157371 | 0.01157371 |
| V | 5000.6 | $K_\alpha$ | 0.01212541 | 0.01212541 |
| Fe | 6392.1 | $K_\alpha$ | 0.05345816 | 0.07227389 |
|  | 7053.1 | $K_\beta$ | 0.01881573 |  |
| Ni | 7428.8 | $K_\alpha$ | 0.01790074 | 0.03845185 |
|  | 8284.5 | $K_\beta$ | 0.02055111 |  |
| Cu | 8049.4 | $K_\alpha$ | 0.02050421 | 0.04103783 |
|  | 8885.8 | $K_\beta$ | 0.02053362 |  |
| Re | 8654.5 | $L_\alpha$ | 0.01994138 | 0.04075005 |
|  | 10177.1 | $L_\beta$ | 0.02080867 |  |
| As | 10529.5 | $K_\alpha$ | 0.02625251 | 0.02625251 |
| Kr | 12561.5 | $K_\alpha$ | 0.06747715 | 0.19714739 |
|  | 14075.6 | $K_\beta$ | 0.12967025 |  |
| Y | 14911.6 | $K_\alpha$ | 0.22241177 | 0.22241177 |
| Te | 27383.2 | $K_\alpha$ | 0.02256075 | 0.02256075 |

Turning back to FIG. 4, the control system 304 may be configured and operable for data communication with an internal and/or external processor and analyzer 306 to generate an output signal indicative of whether the received detected radiation signature of the diamond satisfies a matching condition with natural elemental ID assigned to unique material composition of said diamond and recorded in the diamond certificate.

Thus, the storage device 400 stores a novel database, which is configured according to the invention to be accessible (e.g. via a communication network) and includes a plurality of electronic certificates assigned to a respective plurality of diamonds or plurality of groups of diamonds. Each such electronic certificates includes a natural elemental ID read from the precious stone and assigned to unique material composition of the respective precious stone (e.g. diamond) or group of precious stones (diamonds) and data indicative of a corresponding unique radiation signature of the precious stone or group of precious stones.

The authentication system 300 (which may be equipped with an appropriate communication utility for data communication with various electronic devices, e.g. via a communication network) has access to the storage device 400 and is configured and preprogrammed to be responsive to an input request signal/data (e.g. received via communication network) containing data indicative of a radiation signature (measured by the reading unit) and/or the material composition, to access the storage device 400 and identify whether the received radiation signature and/or material composition has its respective diamond or group of diamonds stored in the database to thereby provide the resulting authentication related signal/data.

It should be noted that the radiation source 302A, the detector 302B and the controller 304 may be constructed as a single device such as an XRF analyzer (for example, Energy Dispersive XRF analyzer), which may be handheld or portable XRF analyzer, or a benchtop XRF spectroscopy device. Alternatively, the emitter, the detector and the controller may be constructed as separate devices. The authentication system 300 may be configured as either of-the-shelf device or alternatively as a device which is specifically designed and constructed for exciting and detecting a response signal from the precious stone.

The controller 304 controls the operation of the emitter 302A and the detector 302B. The processor 306 may be a module of the controller 304, or a module of the detector, or its functional utilities may be distributed in the controller and detector. The processor 306 receives the response X-ray signal (or data indicative thereof) from the detector and processes it so as to filter out the background radiation noise and clutter from the response signal. The processor 306 may employ common filtration methods such as for example quasi-Gaussian spectroscopy amplifier and Gaussian filtering. Additionally, the processor may employ more advanced methods for processing the response signal, for example statistical methods such as time series analysis in order to obtain an enhanced response signal with an improved SNR and SCR.

The processor 306 may determine, according to the response signal (or the enhanced response signal), the concentrations of the markers present on the surface of the precious stone. The processor may also be configured to compare the measured concentrations with the concentrations derived from the preselected code which is stored in the database, and determine its authenticity accordingly.

Turning back to FIGS. 2A and 2B, the technique of the present invention allows for assigning to a diamond a certificate which includes (e.g. in addition to standard parameters of the diamond) data indicative of its unique spectral signature, which may be that of the markings carried by the diamond or may be a natural elemental ID assigned to unique material composition of said diamond. Hence, a customer can receive a diamond kit including a diamond and a certificate assigned to said diamond and comprising data indicative of unique spectral signature, e.g. the natural elemental ID thereof. The diamond can be authenticated by applying the X-ray or gamma-ray inspection thereto as described above to detect its radiation signature indicative of material composition of the diamond, and communicating with the storage device/database to identify whether a match exists between the natural elemental ID in the diamond's certificate and the detected/measured radiation signature.

The signature reading technique and reading system based thereon may for example be as those described in the above-mentioned International application PCT/IL2016/050340, which is assigned to the assignee of the present application and is incorporated herein by reference.

The invention claimed is:

1. A method for marking a precious stone to enable authenticating the precious stone, the method comprising: applying a physical or a chemical material deposition process to the precious stone and creating at least one ultra-thin invisible predetermined marking on at least a portion of a surface of the precious stone, wherein said at least one ultra-thin invisible predetermined marking does not affect appearance or optical properties of said precious stone, said at least one ultra-thin invisible predetermined marking being unique for said precious stone or a batch of related precious stones, such that the precious stone with said at least one ultra-thin invisible predetermined marking is characterized by a unique characteristic X-ray or gamma-ray radiation response to predetermined primary radiation, thereby enabling authentication of the precious stone upon identifying the unique characteristic radiation response of the precious stone.

2. The method of claim 1, wherein said material deposition process comprises at least chemical vapor deposition (CVD).

3. The method of claim 2, wherein said CVD comprises an atomic layer deposition (ALD) process.

4. The method of claim 3, wherein said at least one predetermined marking is in the form of a single- or multi-layer structure.

5. The method of claim 3, wherein said at least one predetermined marking is in the form of a layered structure comprising at least 50 monolayers.

6. The method of claim 5, wherein said at least one predetermined marking is in the form of a layered structure comprising monolayers of platinum interspaced with monolayers of oxygen.

7. The method of claim 6, wherein said layered structure comprises 100 monolayers of platinum interspaced with monolayers of oxygen.

8. The method of claim 1, wherein the unique characteristic X-ray or gamma-ray radiation response is indicative of a unique material composition of said at least one predetermined marking on a structure of the stone, defined by materials and materials' concentrations of the marking and the structure of the stone.

9. The method of claim 1, further comprising recording said at least one predetermined marking being created, said recording comprising applying the predetermined primary radiation to said at least portion of the stone to induce secondary radiation from said at least portion of the stone in response to said primary radiation, and detecting the secondary radiation and storing data indicative thereof as a predetermined characteristic radiation response to be used in an authentication process of the precious stone to identify whether a detected secondary radiation of the precious stone matches the predetermined characteristic radiation response.

10. The method of claim 1, wherein said precious stone is diamond.

11. A method for marking a diamond, having pre-marking appearance and original values of a predetermined set of parameters including carat, clarity, color and cut uniquely characterizing the diamond, to enable authenticating the diamond, the method comprising: applying a physical or chemical material deposition process including atomic layer deposition (ALD) process to the diamond and creating at least one ultra-thin invisible predetermined marking on at least a portion of a surface of the diamond, wherein said at least one ultra-thin invisible predetermined marking does not affect appurtenance or optical properties of the diamond, said at least one ultra-thin invisible predetermined marking being unique for said diamond or a batch of related diamonds, such that the diamond with said at least one predetermined marking being characterized by unique characteristic X-ray or gamma-ray radiation response to predetermined primary radiation, thereby enabling authentication of the diamond upon identifying the unique characteristic radiation response of the diamond, wherein said at least one ultra-thin invisible predetermined marking is in the form of a multi-layered structure covalently bonded to said at least portion of the surface of the diamond, such that the appearance and the values for the predetermined set of parameters are maintained for the diamond carrying said at least one ultra-thin invisible predetermined marking.

* * * * *